US009051589B2

(12) United States Patent
Sato (10) Patent No.: US 9,051,589 B2
(45) Date of Patent: Jun. 9, 2015

(54) PLASMID VECTOR AND TRANSFORMANT STABLY RETAINING PLASMID (75) Inventor: Shunsuke Sato, Takasago (JP)

(73) Assignee: KANEKA CORPORATION, Osaka (JP)

( * ) Notice: Subject to any disclaimer, the term of this patent is extended or adjusted under 35 U.S.C. 154(b) by 1063 days.

(21) Appl. No.: 11/586,574

(22) Filed: Oct. 26, 2006

(65) Prior Publication Data

US 2007/0099281 A1 May 3, 2007

Related U.S. Application Data (60) Provisional application No. 60/754,619, filed on Dec. 30, 2005.

(30) Foreign Application Priority Data

Oct. 27, 2005 (JP) ................. 2005-312921

(51) Int. Cl.
C12P 7/62 (2006.01)
C12N 15/74 (2006.01)
(52) U.S. Cl.
CPC .................. C12P 7/625 (2013.01); C12N 15/74 (2013.01)
(58) Field of Classification Search
CPC ............. C07K 14/415; C07K 2319/00; C12N 15/8289; A23V 2002/00; A23V 2300/21
USPC .......... 435/41, 320.1, 419; 800/274, 278, 287
See application file for complete search history.

(56) References Cited

U.S. PATENT DOCUMENTS

| 4,760,022 A | 7/1988 | Molin et al. |
| 5,670,343 A | 9/1997 | Cameron et al. |
| 5,981,257 A | 11/1999 | Fukui et al. |
| 6,143,518 A | 11/2000 | Cameron et al. |
| 2006/0160195 A1 | 7/2006 | Ono et al. |

FOREIGN PATENT DOCUMENTS

| WO | WO 2004/074476 A1 | 9/2004 |
| WO | WO 2005/098001 A1 | 10/2005 |

OTHER PUBLICATIONS

Score report SEQ ID No. 19, database rge (see reference to Taghavi et al).*
Score report SEQ ID No. 18, database rge (see reference to Taghavi et al).*
Hall et al in Cloning of the *Nocardia corallina* polyhydroxyalkanoate synthase gene and production of poly-(3-hydroxybutyrate-co-3-hydroxyhexanoate) and poly-(3-hydroxyvalerate-co-3-hydroxyheptanoate) in Can. J. Microbiol.1998:vol. 44(7): 687-691; Abstract Only.*
Taghavi et al, Identification of a partition and replication region in the *Alcaligenese eutrophus* megaplasmid pMOL28, Mol. Gen. Genet., 1996, vol. 250, pp. 169-179.
Jackson, Kurt J. et al., "Effects of Recombinant Modulation of the phbCAB Operon Copy Number on PHB Synthesis Rates in Ralstonia eutropha", Journal of Biotechnology, 68 (1999) 49-60.
Haigermoser, C. et al., "Stability of r-microbes: Stabilization of Plasmid Vectors by the Partitioning Function of Broad-Host-Range Plasmid RP4", Journal of Biotechnology, 28 (1993) 291-299.
Lee, S. Y. et al., "Construction of Plasmids, Estimation of Plasmid Stability, and Use of Stable Plasmids for the Production of Poly(3-Hydroxybutyric Acid) by Recombinant *Escherichia coli*", Journal of Biotechnology 32 (1994) 203-211.
Yu, H., et al., "Effect of Poly($\beta$-Hydroxybutyrate) Accumulation on the Stability of a Recombinant Plasmid in *Escherichia coli*", Journal of Bioscience and Bioengineering vol. 96, No. 2, 179-183 (2003).
Vandamme et al, Taxonomy of the genus *Cupriavidus*: a tale of lost and found, Int. J. Syst. Evol. Microbiol. 2004, vol. 54, pp. 2285-2289.
Vaneechoutte et al, *Wautersia* gen. nov., genus accommodating the phylogenetic lineage including *Ralstonia eutropha* and related species, and proposal of *Ralstonia* [*Pseudomonas*] syzygii (Roberts et al. 1990) comb. Nov. Int. J. Syst. Evol Microbiol. 2004, vol. 54 pp. 317-327.
Goris et al, Classification of metal-resistance bacteria from industrial biotopes as *Ralstonia campinensis* sp. nov., *Ralstonia metallidurans* sp. nov. and *Ralstonia basilensis* Steinle et al 1998 emend., Int. J. Syst. Evol. Microbiol 2001, vol. 51, pp. 1773-1782.
Mergeay et al, *Ralstonia metallidurans*, a bacterium specifically adapted to toxic metals: towards a catalogue of metal-responsive genes. FEMS Microbiology Reviews, 2003, vol. 27, pp. 385-410.
Matsumoto et al, Enhancement of poly(3-hydroxybutyrate-co-3-hydroxyvalerate) production in the transgenic *Arabidopsis thaliana* by the in vitro evolved highly active mutants of polyhydroxyalkanoate (PHA) synthase from *Aeromonas caviae*. Biomacromolecules, Jul./Aug. 2005 vol. 6, pp. 2126-2130.
Tsuge et al, Biosynthesis and compositional regulation of poly[(3-hydroxybutyrate)-co-(3-hydroxyhexanoate)] in recombinant *Ralstonia eutropha* expressing mutated polyhydroxyalkanoate synthase genes. Macromolecular Bioscience, 2004, vol. 4, pp. 238-242.

(Continued)

Primary Examiner — Catherine Hibbert
(74) Attorney, Agent, or Firm — Sughrue Mion, PLLC (57) ABSTRACT The object of the present invention is to develop a novel vector. Preferably, the object is to develop a novel vector which can be stably retained in bacteria of the genus *Ralstonia*, *Cupriavidus* or *Wautersia* without any antibiotic-due selective pressure and has no transferability by conjugation. Another object is to provide a strain which can stably produce polyhydroxyalkanoate using the vector, and a method for producing a polyhydroxyalkanoate using the strain. The present invention provides a novel recombinant vector which contains an origin of DNA replication functioning in bacteria of the genus *Ralstonia*, *Cupriavidus* or *Wautersia*. Particularly, the transformant, which is obtained by using a recombinant vector which contains the origin of DNA replication functioning in bacteria of the genus *Ralstonia*, *Cupriavidus* or *Wautersia* and contains a region for a recombinant vector stabilization (par region) can make the vector to be stably retained in bacteria, and can efficiently produce a polyhydroxyalkanoate.

4 Claims, 2 Drawing Sheets (56) References Cited

OTHER PUBLICATIONS

Simon R and Frommer W; Chapter 19: Safety Aspects in Biotechnology; "Biotechnology: Genetic Fundamentals and Genetic Engineering" Biotechnology (Second, Completely Revised Edition); 1993, VCH, ISBN: 3527283129 vol. 2, pp. 835-853 (XP008124163).
European Office Action for counterpart EP Application No. 06822384.1 dated Jul. 19, 2010.
Takeharu Tsuge et al., "Mutation Effects of a Conserved Alanine (Ala510) in Type I Polyhydroxyalkanoate Synthase from *Ralstonia eutropha* on Polyester Biosynthesis", Macromolecular Bioscience, 2004, 4: 963-970.
European Office Action issued Jul. 14, 2011, in counterpart European Patent Application No. 06822384.1 (in the name of Kaneka Corporation).
Simon Silver et al., "Introduction to a special Festschrift issue celebrating the microbiology of *Cupriavidus metallidurans* strain CH34", Antonie van Leeuwenhoek, 2009, 96: 113-114.
Thomas Eitinger et al., "Secondary transporters for nickel and cobalt ions: Theme and variations", BioMetals, 2005, 18: 399-405.
Torsten von Rozycki et al., "Genomic analyses of transport proteins in *Ralstonia metallidurans*", Comparative and Functional Genomics, 2005, 6: 17-56.

* cited by examiner

Fig. 4

# PLASMID VECTOR AND TRANSFORMANT STABLY RETAINING PLASMID

CROSS REFERENCE TO RELATED APPLICATIONS

This application claims benefit of U.S. Provisional Application No. 60/754,619 filed Dec. 30, 2005. This application also claims foreign priority based on Japanese Patent Application No. 2005-312921 filed Oct. 27, 2005.

TECHNICAL FIELD

The present invention relates to a novel vector. The invention also relates to the field of plasmid stabilization and, more particularly, it relates to a recombinant vector capable of being stably retained in bacteria of the genus Ralstonia, Cupriavidus or Wautersia, which are hydrogen bacteria and are known to be PHB-synthesizing bacteria, to a bacterial strain transformed with that vector, and to commercial production of polyhydroxyalkanoates using that bacterial strain.

BACKGROUND ART

When actually applied to the production of a certain desired substance by microorganisms, the recombinant DNA technology generally presents a problem that the recombinant plasmid is unstable.

The cloning and expression vectors generally used in laboratories are mostly multicopy plasmids, and the stable transmission thereof to later generations can be secured by introduction of a number of plasmids per cellular genome (cf. Jones I M et al., Mol. Gen. Genet. 180(3): 579-84 (1980)). However, when a foreign gene is introduced using a plasmid, plasmid elimination occurs during bacterial proliferation cycles, resulting in the instability of the gene introduced. Therefore, in a commercial production process, it is essential to stabilize the plasmid in bacteria until completion of the culture in a fermentor.

So far pJRD215-derived vectors and pBBR-derived vectors have been mainly used as plasmid vectors for gene transfer into bacteria of the genus Ralstonia, Wautersia and Cupriavidus (T. Fukui et al., Biotechnology Letters, Vol. 19, No. 11, November 1997; 1093-97); and Steven Slater et al., Journal of Bacteriology, April 1998: 1979-1987). However, investigations made by the present inventors have revealed that these plasmid vectors become very unstable upon accumulation of polyhydroxyalkanoates, among others, in cells by host bacteria. In the case of a pJRD215-derived vector, for instance, about 80% of the cells after 4 passages under cultivation conditions under which the accumulation of polyhydroxyalkanoates is not rich, without application of any antibiotic-due selective pressure, retain the plasmid, whereas, after 4 passages under cultivation similarly conditions allowing a great accumulation of the polyesters, only 30% of the cells retain the plasmid. The same characteristic feature is presented by pBBR-derived vectors.

These plasmid vectors are broad-host-range vectors developed for use in a wide range of hosts (cf. Luan Tao et al., Metabolic Engineering, Volume 7, Issue 1, January 2005: 10-17; and Davison J et al., Gene, 1987; 51(2-3): 275-80). However, in commercial substance productions using bacteria of the genus Ralstonia, Wautersia or Cupriavidus, for instance, as the hosts, it is necessary to develop plasmid vectors for gene transfer suited for use in bacteria of the genus Ralstonia, Wautersia or Cupriavidus.

Various techniques have so far been developed to stabilize plasmids. However, as regards plasmid vectors capable of being used in the genus Ralstonia, it is only possible to select plasmid-retaining transformants according to the resistance to such a drug as chloramphenicol, kanamycin or ampicillin. When the cultivation is carried out under application of an antibiotic-due selective pressure, the following problems arise: (1) the use of an antibiotic-resistant strain may possibly involve risk to the environment, (2) the amount of an antibiotic which is required during cultivation significantly increases the cost of production, and (3) the use of antibiotics is undesirable for the production of substances to be used in the treatment of humans and animals. Thus, transformants retaining a plasmid owing to drug resistance cannot be applied to commercial production.

In addition to the technique comprising applying an antibiotic-due selective pressure, the so-called par system is known as a system for stable retention of a plasmid (cf. M. Gerlitz et al., Journal of Bacteriology, November: 6194-6203 (1990); and B. Youngren et al., Journal of Bacteriology, July: 3924-3928 (2000)). When the par system works, the plasmids replicated are partitioned among daughter cells, so that a bacterial strain stably retaining a plasmid can be obtained without applying any selective pressure due to antibiotic resistance. Thus, a vector with the par system of the RP4 plasmid, which is usable in Escherichia coli, inserted therein (cf. U.S. Pat. No. 6,143,518) and a vector in which the par region of the R1 plasmid is utilized (cf. U.S. Pat. No. 4,760,022) have so far been developed. Further, it is also known that, in the par region of the megaplasmid pMOL28 retained in the Cupriavidus metallidurans CH34 strain, there occur the promoter parP, the plasmid stabilizing factors parA28 and parB28 and the recognition sequence pars; these genes have already been cloned in the plasmid pSUP202 and the nucleotide sequences thereof have been published (cf. Safieh Taghavi et al., Mol. Gen. Genet. 250: 169-179 (1996)).

As described above, since bacteria belonging to the genus Ralstonia, Cupriavidus or Wautersia (in particular the species Cupriavidus necator) are often used as bacteria for the production of polyhydroxyalkanoates or the production of proteins (cf. Gravin C. et al., Protein Expression & Purification December; 38(2): 64-71 (2004)), it is required to develop a plasmid vector which is particularly usable in these bacteria, has no transferability by conjugation, and is capable of being stably retained therein without any antibiotic-due selective pressure. However, as far as bacteria belonging to the genus Ralstonia, Cupriavidus or Wautersia are concerned, such plasmid stabilization using the par region has not been made as yet; how to construct such system or whether such system is actually effective for plasmid stabilization is unknown.

SUMMARY OF THE INVENTION

It is an object of the present invention to develop a novel vector. More particularly, the object is to develop a vector which can be used preferably in bacteria of the genus Ralstonia, Cupriavidus or Wautersia as the hosts and can be stably retained therein without any antibiotic-due selective pressure. Another object is to cause the resulting transformant to produce a polyhydroxyalkanoate and, further, stabilize the productivity.

DETAILED DESCRIPTION OF THE INVENTION

In constructing a vector capable of being used for transforming desired bacteria of the genus *Ralstonia*, among others, a DNA sequence (ori) is essential for vector replication in host bacteria. Therefore, the present inventors conjectured that by developing a vector which contains an origin of DNA replication (ori) functioning in bacteria of the genus *Ralstonia*, for instance, it might become possible to construct a novel vector which can be used in bacteria of the genus *Ralstonia*, *Cupriavidus* or *Wautersia* as the hosts. The vector to be used for the commercial substance productions is essential to have (1) DNA base pairs the number of which is convenient for handling, (2) no drug-resistance gene for transformant selection, (3) no transferability by conjugation, and the like properties in addition to the property that the vector can be replicated inside host bacteria.

Further, the above-mentioned par system is considered to be very useful as a means for vector stabilization for the reason that antibiotic addition is unnecessary and it is not necessary to introduce any mutation into the chromosome of host bacteria, among others. However, although the above-mentioned megaplasmid pMOL28 can be retained in host bacteria because of the par system thereof, this megaplasmid has such a large number of base pairs as 280 k and no drug-resistance gene. For this reason, this megaplasmid has not been thought to be usable as a vector for bacteria of the genus *Ralstonia*, *Cupriavidus* or *Wautersia*.

Accordingly, the present inventors made intensive investigations in an attempt to solve the above subjects and, as a result, succeeded in developing a novel plasmid vector from the finding that a vector can be stably retained without application of an antibiotic-due selective pressure by causing the origin of replication and the par system of the megaplasmid pMOL28 retained by the *Cupriavidus metallidurans* CH34 strain to function in other hosts than the *Cupriavidus metallidurans* CH34 strain, for example in the species *Cupriavidus necator* (former name: *Ralstonia eutropha*, or *Wautersia eutropha*).

Thus, in a first aspect thereof, the present invention relates to a recombinant vector which contains the sequence identified under SEQ ID NO:18, and contains an origin of replication as introduced therein functioning in bacteria of the genus *Ralstonia*, *Cupriavidus* or *Wautersia* as hosts. It preferably relates to a recombinant vector which has neither the mob gene nor the oriT sequence, namely has no transferability by conjugation, more preferably to a recombinant vector which is obtained from introduction of the par region, which is a DNA region functioning as the par system, namely as a plasmid-stabilizing mechanism, still more preferably to a recombinant vector which contains the DNA fragment identified under SEQ ID NO:19 as the par region, and particularly preferably to a recombinant vector which is derived from any of the recombinant vectors mentioned above by introducing thereinto at least one gene involved in the PHA synthesis as selected from the group of genes consisting of the genes for thiolase and reductase constituting a system for providing 3-hydroxybutyric acid (3HB), the gene for polyhydroxybutyrate (PHB) synthase, namely PHB synthase, the gene for polyhydroxyalkanoate (PHA) synthase, namely PHA synthase, and the genes for acyl-CoA transferase, enoyl-CoA hydratase and acyl-CoA dehydrogenase, which are enzymes in the β oxidation pathway.

In a second aspect, the invention relates to a transformant which is obtained from gene transfer into a host bacterium by means of any of the above-mentioned recombinant vectors, preferably a transformant which is derived from a host cell belonging to the species *Cupriavidus necator*.

In a third aspect, the invention relates to a method for producing a PHA which comprises cultivating the transformant mentioned above and recovering the PHA from the culture.

In the following, the invention is described in detail.

The recombinant vector according to the first aspect of the invention contains an origin of replication as introduced therein, wherein the origin of replication contains the sequence identified under SEQ ID NO:18 and functions in bacteria of the genus *Ralstonia*, *Cupriavidus* or *Wautersia* as hosts.

The origin of replication is a sequence functioning as the origin of replication of the recombinant vector. The sequence shown under SEQ ID NO:18 is a part of the origin of replication (ori region) shown under SEQ ID NO:7 in the megaplasmid pMOL28 retained by the *Cupriavidus metallidurans* CH34 strain. The origin of replication to be introduced into a vector in accordance with the invention may be any one containing the sequence identified under SEQ ID NO:18 and capable of functioning in bacteria of the genus *Ralstonia*, *Cupriavidus* or *Wautersia* as hosts. The sequence shown under SEQ ID NO:7 may be used as the above-mentioned origin of replication.

The recombinant vector of the invention is preferably free of the mob gene group and of the oriT sequence. If the vector has the mob gene group and/or the oriT sequence, transfer by conjugation may occur upon contacting with another microorganism, posing a problem from the safety viewpoint, namely from the viewpoint of transformant containment. Here, the mob gene group refers to a group of genes coding for DNA transferring functions, and the proteins encoded by the mob gene group have a function in making a nick in the oriT sequence and, further, a function in stably transferring a DNA rendered single-stranded. The oriT sequence comprises a nick site and a recognition sequence for nicking.

The recombinant vector of the invention is preferably one resulting from introduction of a vector stabilizing region (par region) functioning as the par system. The par region may be any sequence that can serve as the par system functioning in bacteria of the genus *Ralstonia*, *Cupriavidus* or *Wautersia*. Preferred is, however, the par region in a plasmid retained by a bacterial strain belonging to the genus *Ralstonia*, *Cupriavidus* or *Wautersia* and, more preferably, the par region in the megaplasmid. In the practice of the invention, a DNA fragment containing the sequence defined under SEQ ID NO:19 is most preferably used. The sequence shown under SEQ ID NO:19 is a part of the par region shown under SEQ ID NO:8 in the megaplasmid pMOL28 retained by the *Cupriavidus metallidurans* CH34 strain and contains the parA gene, parB gene and recognition sequence parS.

Since the sequence shown under SEQ ID NO:19 is a part of the par region in the megaplasmid pMOL28 retained by the *Cupriavidus metallidurans* CH34 strain, it is necessary for the desired vector to contain a promoter and a terminator in addition to the sequence shown under SEQ ID NO:19 so that the DNA fragment containing that sequence may function as the par system.

As the promoter, use may be made of the parP in the megaplasmid pMOL28 or a promoter derived from another organism but capable of functioning in bacteria of the genus *Ralstonia, Cupriavidus* or *Wautersia* as hosts. The parP promoter in the megaplasmid pMOL28 is almost identical with the base sequence from the 2388th to 2848th nucleotide in the sequence shown under SEQ ID NO:8.

As the terminator, use may be made of the terminator in the megaplasmid pMOL28 or a terminator derived from another organism but capable of functioning in bacteria of the genus *Ralstonia, Cupriavidus* or *Wautersia* as hosts. The terminator in the megaplasmid pMOL28 is contained in the base sequence from the 61st to the 202nd nucleotide in the sequence shown under SEQ ID NO:8.

The sequence shown under SEQ ID NO:8 may also be used as the par region to be introduced into the recombinant vector of the invention.

The recombinant vector of the invention preferably contains at least one gene involved in the PHA synthesis as introduced therein. Then, the transformant retaining the recombinant vector will be able to efficiently synthesize a PHA if all the genes concerned function effectively. And, in this transformant capable of synthesizing a PHA, unlike multicopy plasmids, the plasmid replicates stably, so that it is possible to stably feed the genes involved in PHA synthesis to hosts for the accumulation of the PHA in commercially significant amounts.

The gene involved in PHA synthesis includes, among others, the genes for thiolase and reductase constituting a 3HB supplying system, the gene for a PHB synthesizing enzyme, namely PHB synthase, the gene for a PHA synthesizing enzyme, namely PHA synthase, and the genes for acyl-CoA transferase, enoyl-CoA hydratase and acyl-CoA dehydrogenase, which are enzymes in the β oxidation pathway. The recombinant vector preferably contains at least one member selected from among those mentioned above as introduced therein. The thiolase is, for example, β-ketothiolase; the reductase is, for example, acetoacetyl-CoA reductase; the PHA synthase is, for example, *Aeromonas caviae*-derived PHA synthase mutant gene, namely N149S/D171G; and the acyl-CoA transferase is, for example, 3-hydroxyacyl-ACP-CoA transferase.

When, in introducing the gene or genes involved in the PHA synthesis into the recombinant vector of the invention, a restriction site or sites are introduced into the vector in advance, it becomes easy to introduce the gene(s) in question.

Further, the recombinant vector of the invention preferably contains a selective marker. While the introduction of the par region into the recombinant vector in accordance with the invention provides the vector with excellent stability and, therefore, no selective pressure due to antibiotic etc. is required, as described later herein, the above-mentioned selective marker can be utilized in transformant selection following transformation of host cells with the recombinant vector of the invention.

The selective marker is not particularly restricted but may be, for example, the kanamycin-, ampicillin-, tetracycline- or like antibiotic-resistance gene. In the recombinant vector of the invention, the kanamycin-resistance gene shown under SEQ ID NO:14 is preferred as the selective marker.

The recombinant vector of the invention may also be a smaller version derived from the recombinant vector obtained after introduction of the above-mentioned gene or genes by rendering the same small-sized.

The recombinant vector can be made small-sized by deleting those portions which are unnecessary for the expression of the origin of replication, the par region, the selective marker and the PHA synthase genes. For example, since the recombinant vector of the invention is preferably free of the mob gene group and the oriT sequence, the size reduction can be realized by deleting such gene group and sequence. When rendered small-sized, the recombinant vector of the invention can be introduced into hosts at an improved transformation ratio.

The recombinant vector of the invention more preferably contains the sequence shown under SEQ ID NO:18 and, further, an origin of replication functioning in bacteria of the genus *Ralstonia, Cupriavidus* or *Wautersia* as hosts and the kanamycin-resistance gene shown under SEQ ID NO:14.

The recombinant vector of the invention, which contains the megaplasmid-derived origin of replication, becomes a recombinant vector capable of functioning also in hosts other than *Cupriavidus metallidurans*.

The vector to be used in constructing the recombinant vector of the invention is not particularly restricted but various plasmids and phages, among others, can be used. In view of the possibility of the resulting recombinant vector serving as a shuttle vector that can replicate in *Escherichia coli* as well, however, the use of an *Escherichia coli*-derived plasmid is preferred.

The method of constructing the recombinant vector of the invention is not particularly restricted but the desired vector can be constructed from any plasmid vector by inserting thereinto the origin of replication functioning in bacteria of the genus *Ralstonia, Cupriavidus* or *Wautersia* as well as a selective marker employed according to need, such as the antibiotic resistance imparting gene (e.g. kanamycin-, ampicillin- or tetracycline-resistance gene) and the par region functioning as the recombinant vector stabilizing par system.

The transformant according to the second aspect of the invention is one obtained by transformation with the above-mentioned recombinant vector. Namely, the transformant of the invention is obtained by introducing the recombinant vector obtained in the above manner into a host bacterial cell displaying competence to the vector.

The host to be used in the practice of the invention is not particularly restricted but may be any of the hosts that can be transformed with the above-mentioned recombinant vector. Thus, use may be made of microorganisms isolated from the nature other than *Cupriavidus metallidurans* and microorganisms deposited with depositories for cultures of microorganisms (e.g. IFO, ATCC), among others. More specifically, use may be made of bacteria of the genus *Ralstonia, Cupriavidus* or *Wautersia, Aeromonas, Escherichia, Alcaligenes* and *Pseudomonas*, among others. Preferred from the safety and productivity viewpoint are bacteria of the genus *Ralstonia, Cupriavidus* and *Wautersia* and, more preferably of the species *Cupriavidus necator*. This species *Cupriavidus necator* is taxonomically identical with *Ralstonia eutropha* and with *Wautersia eutropha* [Vaneechoutte M. et al., Int. J. Syst. Evol. Microbiol., March 54 (Pt2):317-327 (2004); Vadamme P. et al., Int. J. Syst. Evol. Microbiol., November 54 (Pt 6): 2285-2589 (2004)].

The transformant of the invention retains the ori region and a part of the par region of the megaplasmid pMOL28 retained by the *Cupriavidus metallidurans* CH34 strain as introduced thereinto by means of the above-mentioned recombinant vector. Generally, upon introduction into a microorganism retaining a megaplasmid of a gene derived from the megaplasmid, homologous recombination may occur or the introduction of the plasmid containing the same gene may be rejected, so that it is difficult to further introduce a gene in the megaplasmid originally retained by the microorganism into the microorganism. When hosts other than *Cupriavidus metallidurans* are transformed using the above-mentioned recombinant vector in accordance with the invention, however, very high replication ability and stability can be attained presumably due to non-occurrence of competition between the origin of replication in the megaplasmid originally retained by the host and the origin of replication introduced by the recombinant vector, among others, and due to synergy between the replication abilities and stability effects of both.

The method for producing the transformant of the invention is not particularly restricted but the introduction of the recombinant vector into a host can be carried out by any of the methods known in the art. For example, use can be made of the electroporation method (Current Protocols in Molecular Biology, Vol. 1, page 1.8.4, 1994) and the calcium method (Lederberg, E. M. et al., J. Bacteriol., 119, 1072 (1974)). In transformant selection, the selective marker such as the kanamycin resistance expression system etc. can be used. In the practice of the invention, microorganisms other than *Cupriavidus metallidurans* are used as hosts, so that the preliminary procedure for eliminating the megaplasmid from the hosts is unnecessary.

Now, the method of PHA production according to the invention is described.

The PHA to be produced according to the invention is represented by the following general formula (1):

(1)

(in the above formula, R represents an alkyl group containing 1 to 13 carbon atoms and m represents an integer of not smaller than 2. The m R groups may be the same or different).

Preferred as the above PHA is the copolyester P(3HB-co-3HH) constituted of 3-hydroxybutyric acid and 3-hydroxyhexanoic acid monomer units as represented by the general formula (2):

(2)

(in the above formula, n and p each represents an integer of not smaller than 1).

The method of PHA production according to the invention comprises cultivating the transformant mentioned above and extracting and purifying the PHA from the culture. The method referred to just above is not particularly restricted but can be carried out in the following manner.

In the polyhydroxyalkanoate production, the above-mentioned transformant can be cultured using a medium containing such carbon sources as sugar, oil and fat, and/or a fatty acid as well as nutrient sources other than carbon sources, namely a nitrogen source, an inorganic salt and one or more other organic nutrient sources. Thus, for example, a medium containing a carbon source assimilable by the microorganism, optionally with at least one of the nitrogen source, inorganic salt and organic nutrient sources being restricted, for example with the nitrogen source being restricted to 0.01 to 0.1%, can be used as the medium for cultivating the transformant obtained from a host microorganism belonging to the genus *Ralstonia*, *Cupriavidus*, *Wautersia*, *Aeromonas*, *Escherichia*, *Alcaligenes* or *Pseudomonas*, for instance.

As the sugar, there may be mentioned, for example, carbohydrates such as glucose and fructose. As the oil and fat, there may be mentioned oils and fats containing a large amount of saturated and/or unsaturated fatty acids having 10 or more carbon atoms, for example, coconut oil, palm oil, palm kernel oil, and the like. As the fatty acid, there may be mentioned saturated and/or unsaturated fatty acids such as hexanoic acid, octanoic acid, decanoic acid, lauric acid, oleic acid, palmitic acid, linoleic acid, linolenic acid and myristic acid, or derivatives, such as esters and salts, of these fatty acids.

As the nitrogen source, there may be mentioned, for example, ammonia, ammonium salts such as ammonium chloride, ammonium sulfate and ammonium phosphate, peptone, meat extract, yeast extract, and the like. As the inorganic salt, there may be mentioned, for example, potassium dihydrogenphosphate, dipotassium hydrogenphosphate, magnesium phosphate, magnesium sulfate, sodium chloride, and the like. As the other organic nutrient source, there may be mentioned, for example, amino acids such as glycine, alanine, serine, threonine and proline; vitamins such as vitamin B1, vitamin B12 and vitamin C; and the like. Additionally, antibiotics (kanamycin, etc.), which corresponds to the drug-resistance gene existing in the expression vector, may be added into the culture fluid.

The culture may be carried out at any temperature as long as the cells can grow, and preferably at 20 to 40° C. The culture period is not particularly restricted, and may be about 1 to 10 days. Then, PHAs can be recovered from the obtained culture cells.

In the present invention, the PHA recovery from the cells may be carried out by the following methods, for example. After completion of the culture, the cells are separated from the culture fluid using a centrifugal machine, etc., washed with distilled water, methanol, etc., and then dried. From these dried cells, PHAs are extracted using an organic solvent such as chloroform. From the PHA-containing organic solvent solution, cell components are removed by filtration, etc., and a poor solvent such as methanol or hexane is added to the filtrate to precipitate PHAs. Then, the supernatant fluid is removed by filtration or centrifugation, and the obtained PHAs are dried. In such manner, PHAs are recovered.

Analysis of weight average molecular weight (Mw) and 3HH composition (mol %) of the obtained PHAs can be carried out by the gas chromatograph, nuclear magnetic resonance, and the like methods, for example. Alternatively, as a simple method for confirming production of PHAs, a staining method using Nile red can be used. That is, whether polyesters are produced can be confirmed by a method comprising adding Nile red to an agar medium in which recombinant cells grow, culturing the recombinant cells for 1 to 7 days, and observing whether the recombinant cells turn red or not.

The recombinant vector of the invention can be used in bacteria of the genus *Ralstonia*, *Cupriavidus* or *Wautersia* as hosts. When it contains neither the mob gene group nor the oriT sequence, in particular, it has no transferability by conjugation and, further, when it contains the par region introduced therein, it can be stably retained in bacteria without any antibiotic-due selective pressure. Transformants obtained by using that vector can stably produce a PHA.

BEST MODES FOR CARRYING OUT THE INVENTION

The following examples illustrate the present invention more specifically. These examples are, however, by no means limitative of the scope of the invention. The general gene manipulation procedures can be carried out as described in Molecular Cloning (Cold Spring Harbor Laboratory Press (1989)). The enzymes, cloning hosts and other materials to be used in gene manipulation can be purchased from suppliers on the market and can be used according to the instructions given by the suppliers. As for the enzymes, those which can be used in gene manipulation can be used without any particular restriction.

In the following examples, an *Escherichia coli*-derived plasmid was used; this plasmid contains the kanamycin-resistance gene shown under SEQ ID NO:14.

Example 1

Construction of Plasmid Vector pCUP

The plasmid vector for the introduction of an origin of replication and the par region thereinto in this example is not particularly restricted but may be any one capable of being used in bacteria of the genus *Ralstonia*. In the plasmid vector constructed in this example, the origin of replication (SEQ ID NO:7) and the par region given under SEQ ID NO:8 of the megaplasmid (pMOL28) retained by the *Cupriavidus metallidurans* CH34 strain were used. As for the specific construction procedure, a megaplasmid-containing DNA fraction was first prepared from the *Cupriavidus metallidurans* CH34 strain using a DNA purification kit (product of Promega) and, using this DNA fraction as a template and the primers shown under SEQ ID NO:1 and SEQ ID NO:2, a DNA region (about 4 kbp in size) comprising the sequences shown under SEQ ID NO:7 and SEQ ID NO:8 was amplified by the PCR technique. The PCR conditions were: (1) 2 minutes at 98° C.; (2) 30 seconds at 98° C., (3) 30 seconds at 55° C., (4) 5 minutes at 72° C., 30 cycles from (2) to (4); and 5 minutes at 72° C. The polymerase used was TaKaRa Pyrobest DNA Polymerase (product of Takara Bio Inc.). The fragment amplified was cloned in the cloning vector PCR-Blunt 2-TOPO (product of Invitrogen Corporation) for *Escherichia coli*.

Figure 1:
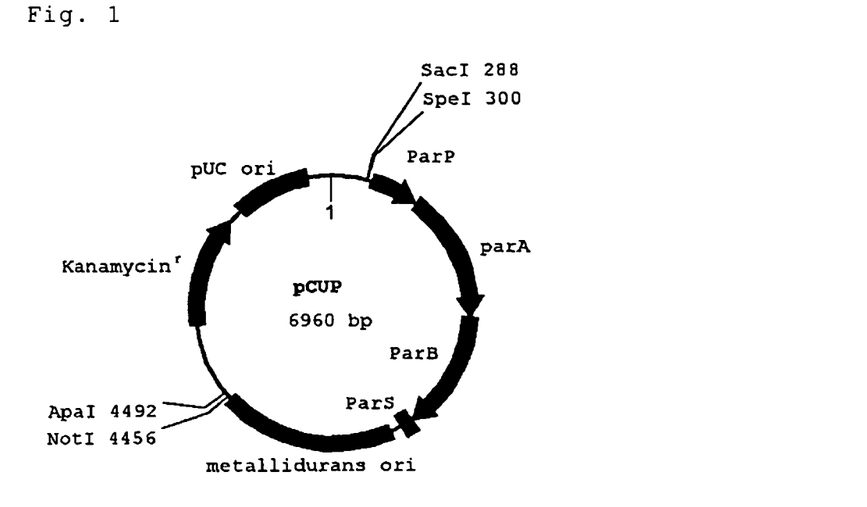
FIG. 1 shows the genes in pCUP and a restriction enzyme map thereof.

Then, using the primers shown under SEQ ID NO:3 and SEQ ID NO:4, the amplification reaction was allowed to proceed outwardly from both ends of the 2061 bp-2702 bp region of the PCR-Blunt 2-TOPO (product of Invitrogen Corporation) by the PCR technique, followed by ligation using a DNA ligase (Ligation High (product of Toyobo Co.)), to give a vector, pCUP, shown in FIG. 1, resulting from deletion of 641 bp. The PCR conditions were: (1) 2 minutes at 98° C.; (2) 30 seconds at 98° C., (3) 30 seconds at 55° C., (4) 7 minutes at 72° C., 30 cycles from (2) to (4); and 7 minutes at 72° C. The polymerase used was TaKaRa Pyrobest DNA Polymerase (product of Takara Bio Inc.).

Example 2

Construction of Plasmid Vector pCUP2

Figure 2:
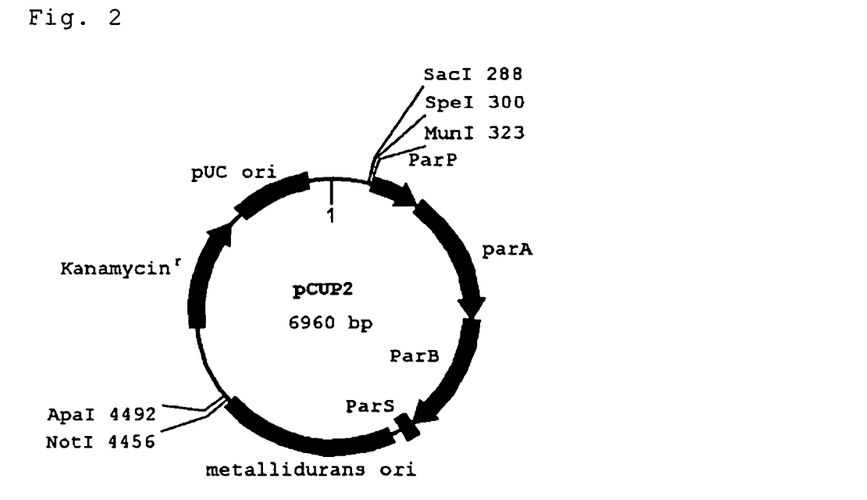
FIG. 2 shows the genes in pCUP2 and a restriction enzyme map thereof.

For facilitating gene transfer using the plasmid vector of the invention, a restriction enzyme MunI site was further introduced into pCUP obtained in Example 1. As for the specific construction procedure, the PCR was carried out by the PCR technique using pCUP constructed in Example 1 as a template and the primers shown under SEQ ID NO:5 and SEQ ID NO:6, followed by ligation of the amplified fragment using a DNA ligase (Ligation High (product of Toyobo Co.)), whereby pCUP2 shown in FIG. 2 was constructed with a MunI introduced therein. The PCR conditions were: (1) 2 minutes at 98° C.; (2) 30 seconds at 98° C., (3) 30 seconds at 55° C. and (4) 5 minutes at 72° C., 30 cycles from (2) to (4). The polymerase used was TaKaRa Pyrobest DNA Polymerase (product of Takara Bio Inc.).

Thus was constructed a plasmid vector containing the DNA region identified under SEQ ID NO:18 and the DNA region identified under SEQ ID NO:19 and free of such genes involved in transfer by conjugation as the mob gene group and the oriT sequence.

Example 3

Transformant Production Using Plasmid Vector pCUP2

The transformation was carried out by the electroporation technique in the following manner. The gene transfer apparatus used for electroporation was the Gene Pulser produced by Bio-Rad Laboratories, Inc., and the cuvette used was Bio-Rad's one with a gap of 0.2 cm. Competent cells (400 µl) of the *Ralstonia eutropha* H16 strain and 5 µl of a plasmid pCUP2 solution prepared were poured into the cuvette, which was then set in the pulser. Electric pulses were applied under the following conditions: electrostatic capacity 25 µF, voltage 1.5 kV, resistance value 800Ω. After pulse application, the bacterial suspension in the cuvette was subjected to 3 hours of shake culture in a nutrient broth medium (product of DIFCO Laboratories) at 30° C., followed by 2 days of cultivation on selective plates (nutrient agar medium (product of DIFCO Laboratories), 100 mg/L of kanamycin) at 30° C., to give a transformant strain.

Comparative Example 1

Transformant Production Using Plasmid Vector pJRD215

Using the plasmid vector pJRD215 containing neither the sequence shown under SEQ ID NO:18 nor the par region, a transformant strain was obtained in the same manner as in Example 3 except that pJRD215 was used as the plasmid.

Example 4

Plasmid Retention Rate in Transformant Obtained by Using Plasmid Vector pCUP2

The transformant strain obtained in Example 3 was tested for plasmid retention rate. The test was performed in the following manner. A culture fluid obtained by 24 hours of cultivation of the transformant obtained in Example 3 using the plasmid vector pCUP2 on an MB+meat extract medium comprising 1% (w/v) of meat extract, 1% (w/v) of Bacto-Trypton, 0.2% (w/v) of yeast extract, 0.9% (w/v) of $Na_2PO_4$/$12H_2O$ and 0.15% (w/v) of $KH_2PO_4$, pH 6.8, with kanamycin (50 mg/L) added was transferred, in an amount of 1% (v/v), to a kanamycin-free MB+oil medium comprising 1.1% (w/v) of $Na_2PO_4\cdot12H_2O$, 0.19% (w/v) of $KH_2PO_4$, 1.29% (w/v) of $(NH_4)_2SO_4$, 0.1% (w/v) of $MgSO_4/7H_2O$, 2.5% (w/v) of palm W olein oil and 0.5% (v/v) of a trace metal salt solution (prepared by dissolving 1.6% (w/v) of $FeCl_3.6H_2O$, 1% (w/v) of $CaCl_2.2H_2O$, 0.02% (w/v) of $CoCl_2.6H_2O$, 0.016% (w/v) of $CuSO_4.5H_2O$, and 0.012% (w/v) of $NiCl_2.6H_2O$ in 0.1 N hydrochloric acid), followed by 24 hours of shake culture. This culture was passaged 3 times at 24-hour intervals and, after 24 hours of cultivation of the 4th generation, the plasmid retention rate was measured in the following manner.

First, the culture fluid was $10^8$-fold diluted with sterile water, the dilution was distributed, in 10- to 100-µl portions, onto plates (nutrient agar medium (product of DIFCO Laboratories)) without addition of kanamycin, the colonies obtained (100 colonies selected at random) were further replicated onto selective plates (nutrient agar medium (product of DIFCO Laboratories)) supplemented with kanamycin (100 mg/L), and the colonies that had grown were counted. In view of the fact that only the bacteria retaining the plasmid can form colonies on the plates, the number of drug-resistance colonies was taken as an indicator of stability. The results thus obtained are shown in Table 1.

Comparative Example 2

Plasmid Retention Rate in Transformant Obtained by Using Plasmid Vector pJRD215

A plasmid retention rate test was carried out in the same manner as in Example 4 except that the transformant obtained in Comparative Example 1 was used as the transformant in lieu of the transformant obtained in Example 3 using the plasmid vector pCUP2. The results are shown in Table 1.

TABLE 1

| | Microorganism | |
|---|---|---|
| | R. eutropha H16 | R. eutropha H16 |
| Plasmid | pCUP2 | pJRD215 |
| Number of colonies | 98 | 32 |
| Retention rate | 98% | 32% |

Example 5

Construction of Plasmid Vector for PHA Synthase Transfer

Figure 3:
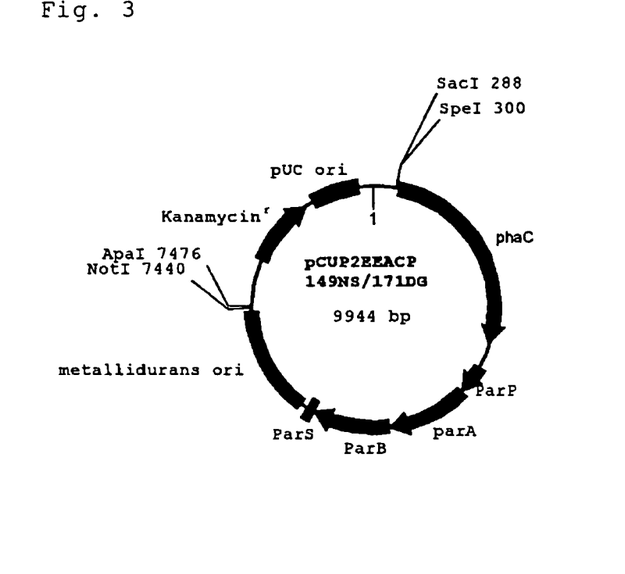
FIG. 3 shows the genes in pCUP2EEACP149NS/171DG and a restriction enzyme map thereof.

An expression plasmid vector (pCUP2EEACP149NS/171DG) was constructed by inserting, into the plasmid vector (pCUP2) obtained in Example 2, the N149S/D171G mutant, which is an *Aeromonas caviae*-derived PHA synthase mutant gene identified under SEQ ID NO:13, as prepared by EcoRI treatment, at the restriction enzyme MunI site of pCUP2 (FIG. 3).

The *Aeromonas caviae*-derived PHA synthase mutant gene, namely the N149S/D171G mutant, was constructed in the following manner. First, pBluescript II KS(−) (product of Toyobo Co.) was treated with PstI, followed by blunting using a DNA blunting kit (product of Takara Bio Inc.) and further followed by ligation, to give a plasmid, pBlue-New, defective in the PstI site. At the EcoRI site of this plasmid, there was cloned the d13 fragment excised from pJRD215-EE32d13 (Japanese Kokai Publication Hei-05-93049) with the same enzyme (to give pBlue-d13). Then, using the clone E2-50-derived plasmid (Kichise et al., Appl. Environ. Microbiol., 68:2411-2419 (2002)) as a template and the set of the primers shown under SEQ ID NO:9 and SEQ ID NO:10 or the set of the primers shown under SEQ ID NO:11 and SEQ ID NO:12, two fragments were respectively obtained by amplification by the PCR technique. The conditions were: (1) 2 minutes at 94° C.; (2) 30 seconds at 94° C., (3) 30 seconds at 55° C., (4) 2 minutes at 72° C., 25 cycles from (2) to (4); and 5 minutes at 72° C. Equimolar amounts of the two amplified fragments were mixed together, and the PCR reaction was again carried out to join the two fragments together. The conditions were: (1) 5 minutes at 96° C.; (2) 2 minutes at 95° C., (3) 1 minute at 72° C., 12 cycles from (2) to (3). The polymerase used was Pyrobest DNA Polymerase (product of Takara Bio Inc.). A DNA fragment having the desired size was excised from an agarose electrophoretic gel, treated with PstI and XhoI and cloned in pBlue-d13 treated with the same enzymes in a manner of fragment interchange (to give pBlue-N149S/D171G). The base sequence analysis was carried out using a Perkin Elmer Applied Biosystems DNA sequencer, 310 Genetic Analyzer; it was confirmed that the gene in question is a mutant gene coding for serine in lieu of the 149th amino acid asparagines and for glycine in lieu of the 171st amino acid aspartic acid of the PHA synthase.

The pBlue-N149S/D171G prepared in the above manner was treated with the restriction enzyme EcoRI and joined to pCUP2 treated with the restriction enzyme MunI using a DNA ligase (Ligation High, product of Toyobo Co.). A PHA synthase gene-containing plasmid vector, pCUP2EEACP149NS/171DG, was thus constructed.

Example 6

Construction of Plasmid Vector for Enoyl-CoA Hydratase Gene Transfer

Figure 4:
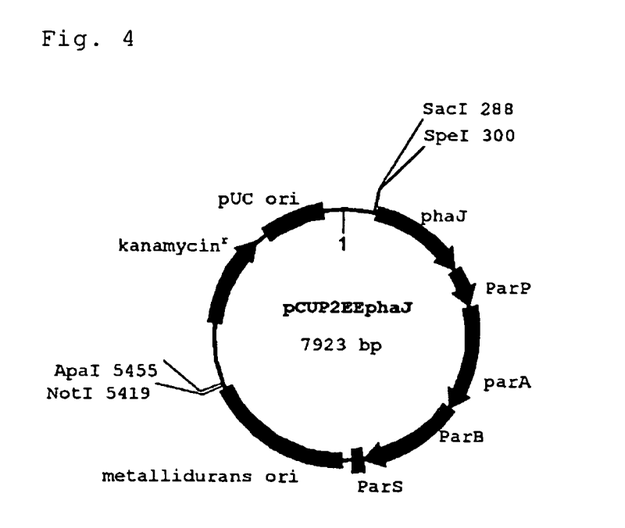
FIG. 4 shows the genes in pCUP2EEphaJ and a restriction enzyme map thereof.

An expression plasmid vector (pCUP2EEphaJ) was constructed by inserting the *Aeromonas caviae*-derived enoyl-CoA hydratase gene shown under SEQ ID NO:17 as prepared by EcoRI treatment into the plasmid vector obtained in Example 2 (pCUP2) at the restriction enzyme MunI site of pCUP2 (FIG. 4). This vector was constructed in the following manner.

First, using, as a template, pJRD215-EE32 (Japanese Kokai Publication Hei-05-93049) containing the enoyl-CoA hydratase gene to be used in the practice of the invention, together with the set of the primers shown under SEQ ID NO:15 and SEQ ID NO:16, an amplified fragment containing the enoyl-CoA hydratase gene shown under SEQ ID NO:17 was obtained by amplification using the PCR technique. The conditions were: (1) 2 minutes at 94° C.; (2) 10 seconds at 98° C., (3) 10 seconds at 60° C., (4) 1 minutes at 68° C., 30 cycles from (2) to (4); and 3 minutes at 68° C. The polymerase used was LA Taq DNA Polymerase (product of Takara Bio Inc.). Then, this amplified fragment was treated with BglII and AflII and subjected to ligation treatment with pJRD215-EE32d13 treated in the same manner with BglII and AflII and then treated with alkaline phosphatase for DNA dephosphorylation treatment; thus, cloning was effected in a manner of replacement of the DNA fragment between the BglII and AflII sites of pJRD215-EE32d13 (to give pJRD215-EEphaJ). Ligation High (product of Toyobo Co.) was used for the ligation. A DNA fragment containing the enoyl-CoA hydratase gene was prepared from the thus-constructed pJRD215-EEphaJ by treatment with EcoRI and ligated with pCUP2 treated with MunI to give pCUP2EEphaJ (FIG. 4). Ligation High (product of Toyobo Co.) was used for the ligation.

Example 7

Transformant Production Using Plasmid Vector for PHA Synthase Transfer

A transformant retaining a plasmid vector for PHA synthase transfer was produced in the same manner as in Example 3 except that a solution prepared from the plasmid vector for PHA synthase transfer (pCUP2EEACP149NS/171DG) obtained in Example 5 was used in lieu of the plasmid pCUP2 solution. The *Ralstonia eutropha* PHB4 strain (Tsuge, T. et al., Macromol. Biosci., October 20; 4(10):963-70 (2004)) incapable of PHA synthesis was used for the transformation.

Example 8

Transformant Production Using Plasmid Vector for Enoyl-CoA Hydratase Transfer A transformant retaining a plasmid vector for enoyl-CoA hydratase transfer was produced in the same manner as in Example 3 except that a solution prepared from the plasmid vector for enoyl-CoA hydratase transfer (pCUP2EEphaJ) obtained in Example 6 was used in lieu of the plasmid pCUP2 solution. The *Ralstonia eutropha* PHB4 strain incapable of PHA synthesis was used for the transformation.

Example 9

Retention Rate of Plasmid Vector pCUP2EEACP149NS/171DG in Transformant

Plasmid retention rate testing was carried out in the same manner as in Example 4 except that the transformant strain obtained in Example 7 was used as the transformant in lieu of the transformant strain obtained in Example 3 by using the plasmid vector pCUP2. The results are shown in Table 2.

TABLE 2

|  | Microorganism | | |
| --- | --- | --- | --- |
|  | *R. eutropha* PHB-4 | *R. eutropha* PHB-4 | *R. eutropha* PHB-4 |
| Plasmid | pCUP2EEACP149NS/171DG | pCUP2EEphaJ | pJRD215 |
| Number of colonies | 95 | 96 | 30 |
| Retention rate | 95% | 96% | 30% |

Example 10

Retention Rate of Plasmid Vector pCUP2EEphaJ in Transformant

Plasmid retention rate testing was carried out in the same manner as in Example 4 except that the transformant strain obtained in Example 8 was used as the transformant in lieu of the transformant strain obtained in Example 3 by using the plasmid vector pCUP2. The results are shown in Table 2.

Comparative Example 3

Transformant Production Using Plasmid Vector pJRD215 and the *Ralstonia eutropha* PHB4 Strain as Host A transformant retaining a plasmid vector pJRD215 was produced in the same manner as in Example 3 except that the pJRD215 containing neither the sequence shown under SEQ ID NO:18 nor the par region as the plasmid, and using the *Ralstonia eutropha* PHB4 strain as the host.

Comparative Example 4

Retention Rate of Plasmid Vector pJRD215, Retained in the *Ralstonia eutropha* PHB4 Strain as Host, in Transformant Plasmid retention rate testing was carried out in the same manner as in Example 4 except that the transformant strain obtained in Example 3 was used as the transformant in lieu of the transformant strain obtained in Example 3 by using the plasmid vector pCUP2. The results are shown in Table 2.

Example 11

Polyester Production in Transformant Strain Obtained in Example 7

A Nile red-containing medium (9 g of disodium hydrogen phosphate dodecahydrate, 1.5 g of potassium dihydrogen phosphate, 0.05 g of ammonium chloride, 0.02 g of magnesium sulfate heptahedrate, 0.5 g of fructose, 0.25 ppm of cobalt chloride hexahydrate, 16 ppm of iron (III) chloride hexahydrate, 10.3 ppm of calcium chloride dihydrate, 0.12 ppm of nickel chloride hexahydrate, 0.16 ppm of copper sulfate pentahydrate, 0.5 mg of Nile red, 15 g/L of agar) was seeded with cells of the transformant obtained in Example 7, and cultivation was carried out at 30° C. for 2 days. As a result, the colonies turned red; thus, the polyester accumulation in bacterial cells could be confirmed.

INDUSTRIAL APPLICABILITY

The plasmid vector of the invention can be used in bacteria of the genera *Ralstonia*, *Cupriavidus* and *Wautersia* as hosts. When it contains neither the mob gene group nor the oriT sequence, in particular, it has no transferability by conjugation and, further, when it contains the par region introduced therein, it can be stably retained in bacteria without any antibiotic-due selective pressure. Transformants obtained by using that vector can stably produce a PHA.

The invention claimed is:

1. A host bacterium transformant comprising a recombinant vector,
   wherein the host bacterium belongs to the species *Cupriavidus necator*,
   wherein the recombinant vector has neither a mob gene nor an oriT sequence, and
   wherein the recombinant vector contains a vector stabilizing region which is a par region functioning as a par system, and
   wherein the recombinant vector contains the sequence of SEQ ID NO: 18 as a part of an origin of replication, and
   wherein the recombinant vector comprises, as introduced therein, at least one gene involved in polyhydroxyalkanoate synthesis selected from the group consisting of a gene for thiolase, a gene for reductase, a gene for polyhydroxybutyrate synthase, a gene for polyhydroxyalkanoate synthase, a gene for acyl-CoA transferase, a gene for enoyl-CoA hydratase, and a gene for acyl-CoA dehydrogenase, and
   whereby the vector has no transferability by conjugation.

2. The transformant according to claim 1,
   wherein the par region comprises the sequence identified under SEQ ID NO:19.

3. A method for producing a polyhydroxyalkanoate which comprises cultivating the transformant according to claim 1, and recovering and purifying the polyhydroxyalkanoate from the culture.

4. The method for producing a polyhydroxyalkanoate according to claim 3 wherein the polyhydroxyalkanoate is a copolyester constituted of 3-hydroxybutyric acid and 3-hydroxyhexanoic acid monomer units.

* * * * *

SEQUENCE LISTING

<160> NUMBER OF SEQ ID NOS: 19

<210> SEQ ID NO 1
<211> LENGTH: 20
<212> TYPE: DNA
<213> ORGANISM: Artificial Sequence

```
<220> FEATURE:
<223> OTHER INFORMATION: chemically-synthesize primer sequence

<400> SEQUENCE: 1
ctttcagcgc aatgtacacc                                              20

<210> SEQ ID NO 2
<211> LENGTH: 20
<212> TYPE: DNA
<213> ORGANISM: Artificial Sequence
<220> FEATURE:
<223> OTHER INFORMATION: chemically-synthesize primer sequence

<400> SEQUENCE: 2
ctgtacacgc ctcaaaagga                                              20

<210> SEQ ID NO 3
<211> LENGTH: 20
<212> TYPE: DNA
<213> ORGANISM: Artificial Sequence
<220> FEATURE:
<223> OTHER INFORMATION: chemically-synthesize primer sequence

<400> SEQUENCE: 3
tttcgttcca ctagacgtca                                              20

<210> SEQ ID NO 4
<211> LENGTH: 20
<212> TYPE: DNA
<213> ORGANISM: Artificial Sequence
<220> FEATURE:
<223> OTHER INFORMATION: chemically-synthesize primer sequence

<400> SEQUENCE: 4
cgcatcagga aattgtaagc                                              20

<210> SEQ ID NO 5
<211> LENGTH: 20
<212> TYPE: DNA
<213> ORGANISM: Artificial Sequence
<220> FEATURE:
<223> OTHER INFORMATION: chemically-synthesize primer sequence

<400> SEQUENCE: 5
ccagtgtgct gcaattggcc                                              20

<210> SEQ ID NO 6
<211> LENGTH: 20
<212> TYPE: DNA
<213> ORGANISM: Artificial Sequence
<220> FEATURE:
<223> OTHER INFORMATION: chemically-synthesize primer sequence

<400> SEQUENCE: 6
ccgttactag tggatccgag                                              20

<210> SEQ ID NO 7
<211> LENGTH: 1223
<212> TYPE: DNA
<213> ORGANISM: Cupriavidus metallidurans

<400> SEQUENCE: 7
tgtacaccct aggccatggc atgagcattg ttcgtcgtgt tgccgcgtt ggctgacctg     60 cggtcgcgca gcatcgctcg caacgccgat aacgtcgaag ccgcctcctt tccccgtttc   120
```

```
tcgagccggc cgcttgctct ctggggagca gcgtagacct cagctttctg gtacgcacca      180
gcgtgtagtc gccttgcaaa ttcggcgagg gaagttccta ccaagcggga agtgaccgca      240 cttttggacct cggtgacaag cactgagctt ccgtcgcttt cgacttcgaa atggttgcct    300
ttttcgtcca cgaaacactg ccgcgctgcc cctgcgagta tcgaacgcac gaaatcgcgg      360
tcctgcactt ggattcgggc tttgtcttct ttgagtgcct ttgctttgca gacagcactg      420
aaatcggtgc gggcggtgag tagggcaagc agatacgctt ttggcacgcg tgctttcgca      480
agactctccc atgtcgcgct tacgacatct gagagaaagt ggccttgctc tttagccttt      540
cgcatcaacc aaaaaattaa atttacatca gacccaggc cgcgcagacg tgtcaggtcc       600
tgggggagcc gatcctgctg tcttttttga aaggagtatg ggacacgatc ttctgtaaac      660
aggactctcg ttttgagaga cggttgcgcc atagaagagg gtggtggaac ggccggctcg      720
ccgagctgcg ctgtgtcgtc ctcgcccgta cccgtggttt cttcttcttt tcgcgagctt     780
aagccgagca tctccgtcgc ttttccgtc aggtaaatgt aggctcctgc gaatcggcca      840
aatcgcttcc gaacttgaac gtcgacggta attaggccca agtcgagcag ttctcgttga     900
gcacggtacc aagtagccgg cgacattccg gtttcggcac aaagcgtttc ccggtgctta    960
aagatcttac cggtggggtc atcgttattc gccgtgcggg cgagggcggc aagagctgat     1020
cgggcgctac gcccgatccc gacgattcga gttgcgcgct cgactgcttc gatagtcttg    1080
cgtttgaggc gcttgggcgc cggagcaatc agagcgtctg tctggttaag gtgttttttgt    1140 gggcgagcaa catcctcgcc agcaacggag cgttgcgcga aagtcatatg accttcccat    1200
tcgtaaaaaa tggttgaagt cgc                                               1223

<210> SEQ ID NO 8
<211> LENGTH: 2848
<212> TYPE: DNA
<213> ORGANISM: Cupriavidus metallidurans

<400> SEQUENCE: 8
ttgactcagg ttcgcgttcc gctacactcc gactaacgaa tccatgtcga gtggcttcgg      60
tgtgtagcgg cccgggaaact ggtcagcttg aagttctcaa aagcccacgg ttgccgccgt    120 ggcttttgt ttttgtagga ttacagtcta gacatggctt aaaacctcga ttcgtagtac       180
gaagtcctta aaaacaagc acttagcttt ttgcgtcttc cgacgcagct ttagctaacc      240
cttccagatg ttcgcgaatg gccgattggg ccgcttccgc ttcttcctcg ctgcggaact     300
caatgcgcat gactttcttt gcgatacgaa catcgcacca agtcgccttt ccgccttga     360 ttttgaagcc ggtagatgcg gcaggcctgg tcttaacctg ctcggcctta gtcatccgta    420
cggcctgctg ttgatcgatc ttcttctcgg ccaacaactt aaccgcttcg acgacccgat     480
ccccgcgacc gtctttggtc gcccttgcca actcggcgcc agcattcgac ccgagcaggt    540
ctgggcggct atcgagaagg cttaggacct cggagggcaa gttccggaac gacaaaatct    600
ctgagagagt cgagacaggt acaccagcct gttcagctat gcggcttga gtcttgtctg     660 ggctgcgaag cagcagttcg tcgaacttcc gaaacttctc gaaatccgtt aaatctgact    720
gcataaggtt cgcgtagaac gcgcccgtgt cagcctcgtc tgaactaagt tcgccgagca    780
cgcagcgtat gtgatcgcgc ccaagctcgc ggtacgcgtc tgtccggtga tgcccggaga    840
caatctcgaa gcctcccgca ggccgagggc atacaatcac aggatgaacg agcttgttgt    900
gcctgaggtt ttccctcaat tcgacatact tctcggagg catgaagcgt ctgcggcctg      960
ggacctcatg cagttggtcg ataggcacat ccactgcgcc gccgctgacg cgggccgact   1020
```

```
caagttctgc tcttagttgc gcgatctcgt tagcctgtcg ctcaaccttc ccttgcatat    1080
gcattaactg accgggcgca gttcgcggcg cttgcggacc gcgcgcagcg gctttctcca    1140
agtcttccgc cgtgaccttg atgttcccag cctttgcggc aagcttttct ctcaaactca    1200
ttcttcaatt ccttgccaaa gcgcgctgac cttgtcgtcc acatagtcga caaactcatc    1260
gcagggttgg cgaatgcgtc gcatcgtctc ggtgttcgcc tcgctagagg agaggtcata    1320
gaccgtgcga aattgaatgc tgctgttacg ggcgaggtcc gtctcaggga tctcaatcgg    1380
cagcacgcgc gacccataga cgccgcgaat ccagtctgcc accaggcgag gagcgttctt    1440
tttctccatg cgtgtcatga aacatcgag aaagtcgaac tccttttag atccctcgct      1500 ctgctcttcc atgcctgtta ctaggtccga aagagttgc cagaactgga ccatagacgc      1560
gaaagccaag gtgtccggga ccaccggtac gatgacgcca tcggcagcga aaatcgcgtt    1620
gatggtcagg tagctgaggg taggagccgt gtcgaggatg atgtagtcat attcgtcttt    1680
caacgaatcg aggccgttac ttaacacgcg ctcgaacgga atatggcctt cctctgccgt    1740
cgcccgagcc ggaagcataa actccgcgtt gaaaagctca gtagacgaag gaatcaaatc    1800
caggttaggc cagtaagtct cctgaggaag ccctcgcata tcgaaggact cgcccgccaa    1860
atacgcctcg atgagcggca taatggtgtt ttcggacgac acctcggcat gtggattgat    1920
gccatacagc gtggttgcgc ttccctgcgg atccagatca acgtggcaca ccttccgacc    1980
tcgccgcaga ctcaagccct ggcagaggag ggtggacata gtggtcttcg tgacaccgcc    2040
cttgaagttc gcaactgcaa tgactttacc tggtcccctt cgcgggacag gcttaagttc    2100
cgctcggatc cattgcattg cctcgctgag gctgaaatag cgcactgcac cgggtcgcga    2160
ttgctggccc tgagggagat ccccttttt gagggaccgg ttcatccgcg ttttgtcgat     2220
gccacacaat tcttgtaggc ggccagacgg gatcagcggg gcttccttcc gaggaaatgg    2280
ctccagcatc tcatcccgaa ttttctgcag catcaccgcg gagagatttg ccaactgctt    2340
caaatcctca ggcgtcgtct tgctggggtg ggctagcttg atatccattc ggttcaaaaa    2400
cctttaagct gttcaccgga accgccggtg gatcgtgcaa ccgttttcgg caaaaatgac    2460
gtccgcggtt gcgttgccgt gaaggttagc ggcccttaga cgtatacgca agttaacttt    2520
gtgcctgttg tacccgagag atcgagctgt tccccggta cttacgggtc gttgttaaag     2580
taaaaggcga ggaattctac gaaagtgcca tataacgcac aaagaatgcg cgcctcagga    2640
agtaaggctt aggccagcct caaggacgaa gcgcgaggtc gggttcttct tcgccgttga    2700
gataaacagg caatccctgg cgcgcgtgac ggcgactag aagaggcgcc tttcttcgct     2760
ttctgggctt tcgctgtcgg gaacgattgt ctcttcggct cggactatgg ctacgctgtc    2820
ccactcccgt ccttttgagg cgtgtaca                                       2848
```

<210> SEQ ID NO 9
<211> LENGTH: 26
<212> TYPE: DNA
<213> ORGANISM: Artificial Sequence
<220> FEATURE:
<223> OTHER INFORMATION: chemically-synthesize primer sequence

<400> SEQUENCE: 9
aggttctggc cgccggactc cagggt                                         26

<210> SEQ ID NO 10
<211> LENGTH: 32
<212> TYPE: DNA

<213> ORGANISM: Artificial Sequence
<220> FEATURE:
<223> OTHER INFORMATION: chemically-synthesize primer sequence

<400> SEQUENCE: 10
ggagagcata tgagccaacc atcttatggc cc					32

<210> SEQ ID NO 11
<211> LENGTH: 26
<212> TYPE: DNA
<213> ORGANISM: Artificial Sequence
<220> FEATURE:
<223> OTHER INFORMATION: chemically-synthesize primer sequence

<400> SEQUENCE: 11
accctggagt ccggcggcca gaacct					26

<210> SEQ ID NO 12
<211> LENGTH: 55
<212> TYPE: DNA
<213> ORGANISM: Artificial Sequence
<220> FEATURE:
<223> OTHER INFORMATION: chemically-synthesize primer sequence

<400> SEQUENCE: 12
atggatcctg cagttagtgg tggtggtggt ggtgtgcggc gtcctcctct gttgg					55

<210> SEQ ID NO 13
<211> LENGTH: 2377
<212> TYPE: DNA
<213> ORGANISM: Artificial Sequence
<220> FEATURE:
<223> OTHER INFORMATION: chemically-synthesize PHA synthase

<400> SEQUENCE: 13
gaattccgat ctggaccggg gtgctggcct gggccacgcc ggcgagggcc agcgcggagc					60
aaccgagcag cagggcgaga ggtttcatcg ggattccttg cagtctgaa tgacgtgcca					120
gcctatcagc gcggcgccgg tgcggcgagg gcgcgccgga cccagtgcgt cacctctcgt					180
ctgatccgcc tccctcgacg ggcgtcgctg acaaaaaaat tcaaacagaa attaacattt					240
atgtcattta caccaaaccg catttggttg cagaatgctc aaacgtgtgt ttgaacagag					300
caagcaacac gtaaacaggg atgacatgca gtacccgtaa aagggccga ttggcccaga					360
tctcgcctcg ggtgtgggtg aaggagagca catgagccaa ccatcttatg cccgctgtt					420
cgaggccctg gccactaca atgacaagct gctggccatg gccaaggccc agacagagcg					480
caccgcccag gcgctgctgc agaccaatct ggacgatctg ggccaggtgc tggagcaggg					540
cagccagcaa ccctggcagc tgatccaggc ccagatgaac tggtggcagg atcagctcaa					600
gctgatgcag cacaccctgc tcaaaagcgc aggccagccg agcgagccgg tgatcacccc					660
ggagcgcagc gatcgccgct tcaaggccga ggcctggagc gaacaaccca tctatgacta					720
cctcaagcag tcctacctgc tcaccgccag gcacctgctg gcctcggtgg atgccctgga					780
gggcgtcccc cagaagagcc gggagcggct gcgtttcttc acccgccagt acgtcagcgc					840
catggcccc agcaacttcc tggccaccaa cccgagctg ctcaagctga ccctggagtc					900
cggcggccag aacctggtgc gcggactggc cctcttggcc gaggatctgg agcgcagcgc					960
cgatcagctc aacatccgcc tgaccgacga atccgccttc gagctcgggc gggatctggc					1020
cctgaccccg ggccgggtgg tgcagcgcac cgagctctat gagctcattc agtacagccc					1080
gactaccgag acggtgggca agacacctgt gctgatagtg ccgcccttca tcaacaagta					1140

```
ctacatcatg gacatgcggc cccagaactc cctggtcgcc tggctggtcg cccagggcca    1200
gacggtattc atgatctcct ggcgcaaccc gggcgtggcc caggcccaaa tcgatctcga    1260
cgactacgtg gtggatggcg tcatcgccgc cctggacggc gtggaggcgg ccaccggcga    1320
gcgggaggtg cacggcatcg gctactgcat cggcggcacc gccctgtcgc tcgccatggg    1380
ctggctggcg gcgcggcgcc agaagcagcg ggtgcgcacc gccaccctgt tcactaccct    1440
gctggacttc tcccagcccg gggagcttgg catcttcatc cacgagccca tcatagcggc    1500
gctcgaggcg caaaatgagg ccaagggcat catggacggg cgccagctgg cggtctcctt    1560
cagcctgctg cggagaaaca gcctctactg gaactactac atcgacagct acctcaaggg    1620
tcagagcccg gtggccttcg atctgctgca ctggaacagc gacagcacca atgtggcggg    1680
caagacccac aacagcctgc tgcgccgtct ctacctggag aaccagctgg tgaaggggga    1740
gctcaagatc cgcaacaccc gcatcgatct cggcaaggtg aagacccctg tgctgctggt    1800
gtcggcggtg gacgatcaca tcgccctctg gcagggcacc tggcagggca tgaagctgtt    1860
tggcggggag cagcgcttcc tcctggcgga gtccggccac atcgccggca tcatcaaccc    1920 gccgccgcc aacaagtacg gcttctggca acgggggcc gaggccgaga gcccggagag    1980
ctggctggca ggggcgacgc accagggcgg ctcctggtgg cccgagatga tgggctttat    2040
ccagaaccgt gacgaagggt cagagcccgt ccccgcgcgg gtcccggagg aagggctggc    2100 ccccgcccc ggccactatg tcaaggtgcg gctcaacccc gtgtttgcct gcccaacaga    2160
ggaggacgcc gcatgagcgc aggatccgtg gtcaagctgc cttaagcacc ggcggcacgc    2220
aggcacaatc agcccggccc ctgccgggct gattgttctc ccccgctccg cttgccccct    2280
ttttcggggc aatttggccc aggcccttc cctgccccgc ctaactgcct aaaatggccg    2340
ccctgccgtg taggcattca tccagctaga ggaattc                             2377
```

<210> SEQ ID NO 14
<211> LENGTH: 933
<212> TYPE: DNA
<213> ORGANISM: Artificial Sequence
<220> FEATURE:
<223> OTHER INFORMATION: chemically-synthesized kanamycin resistance
      gene

<400> SEQUENCE: 14

```
ccggaattgc cagctggggc gccctctggt aaggttggga agccctgcaa agtaaactgg     60
atggctttct cgccgccaag gatctgatgg cgcaggggat caagtctctga tcaagagaca    120 ggatgaggat cgtttcgcat gattgaacaa gatggattgc acgcaggttc tccggccgct    180
tgggtggaga ggctattcgg ctatgactgg gcacaacaga caatcggctg ctctgatgcc    240
gccgtgttcc ggctgtcagc gcaggggcgc ccggttcttt ttgtcaagac cgacctgtcc    300
ggtgccctga tgaactgca agacgaggca gcgcggctat cgtggctggc cacgacgggc    360
gttccttgcg cagctgtgct cgacgttgtc actgaagcgg gaagggactg gctgctattg    420
ggcgaagtgc cggggcagga tctcctgtca tctcaccttg ctcctgccga gaaagtatcc    480
atcatggctg atgcaatgcg gcggctgcat acgcttgatc cggctacctg cccattcgac    540
caccaagcga aacatcgcat cgagcgagca cgtactcgga tggaagccgg tcttgtcgat    600
caggatgatc tggacgaaga gcatcagggg ctcgcgccag ccgaactgtt cgccaggctc    660
aaggcgagca tgcccgacgg cgaggatctc gtcgtgaccc atggcgatgc ctgcttgccg    720
aatatcatgg tggaaaatgg ccgcttttct ggattcatcg actgtggccg ctgggtgtg    780
```

```
gcggaccgct atcaggacat agcgttggct acccgtgata ttgctgaaga gcttggcggc    840
gaatgggctg accgcttcct cgtgctttac ggtatcgccg ctcccgattc gcagcgcatc    900
gccttctatc gccttcttga cgagttcttc tga                                 933

<210> SEQ ID NO 15
<211> LENGTH: 75
<212> TYPE: DNA
<213> ORGANISM: Artificial Sequence
<220> FEATURE:
<223> OTHER INFORMATION: chemically-synthesize primer sequence

<400> SEQUENCE: 15
tggcccagat ctcgcctcgg gtgtgggtga aggagagcac atgagcgcac aatccctgga    60
agtaggccag aaggc                                                     75

<210> SEQ ID NO 16
<211> LENGTH: 78
<212> TYPE: DNA
<213> ORGANISM: Artificial Sequence
<220> FEATURE:
<223> OTHER INFORMATION: chemically-synthesize primer sequence

<400> SEQUENCE: 16
gccggtgctt aaggcagctt gaccacggat cctgcgtcat taaggcagct tgaccacggc    60
ttcccccgtc acggcgag                                                  78

<210> SEQ ID NO 17
<211> LENGTH: 453
<212> TYPE: DNA
<213> ORGANISM: Artificial Sequence
<220> FEATURE:
<223> OTHER INFORMATION: chemically-synthesize (R)-specific enoyl-CoA
      hydratase

<400> SEQUENCE: 17
tggcccagat ctcgcctcgg gtgtgggtga aggagagcac atgagcgcac aatccctgga    60
agtaggccag aaggcccgtc tcagcaagcg gttcggggcg gcggaggtag ccgccttcgc    120
cgcgctctcg gaggacttca acccctgca cctggacccg gccttcgccg ccaccacggc    180
gttcgagcgg cccatagtcc acggcatgct gctcgccagc ctcttctccg ggctgctggg    240
ccagcagttg ccgggcaagg ggagcatcta tctgggtcaa agcctcagct tcaagctgcc    300
ggtctttgtc ggggacgagg tgacggccga ggtggaggtg accgcccttc gcgaggacaa    360
gcccatcgcc accctgacca cccgcatctt cacccaaggc ggcgccctcg ccgtgacggg    420
ggaagccgtg gtcaagctgc cttaagcacc ggc                                 453

<210> SEQ ID NO 18
<211> LENGTH: 91
<212> TYPE: DNA
<213> ORGANISM: Cupriavidus metallidurans

<400> SEQUENCE: 18
ctctcccatg tcgcgcttac gacatctgag agaaagtggc cttgctcttt agcctttcgc    60
```
atcaaccaaa aaattaaatt tacatcaaga c                                    91

<210> SEQ ID NO 19
<211> LENGTH: 2291
<212> TYPE: DNA
<213> ORGANISM: Cupriavidus metallidurans

<400> SEQUENCE: 19

```
caaaagccca cggttgccgc cgtgggcttt tgtttttgta ggattacagt ctagacatgg    60
cttaaaacct cgattcgtag tacgaagtcc ttaaaaaaca agcacttagc ttttttgcgtc   120
ttccgacgca gctttagcta acccttccag atgttcgcga atggccgatt gggccgcttc   180
cgcttcttcc tcgctgcgga actcaatgcg catgactttc tttgcgatac gaacatcgca   240
ccaagtcgcc tttcccgcct tgattttgaa gccggtagat gcggcaggcc tggtcttaac   300
ctgctcggcc ttagtcatcc gtacggcctg ctgttgatcg atcttcttct cggccaacaa   360
cttaaccgct tcgacgaccc gatccccgcg accgtctttg tcgcccttg ccaactcggc    420
gccagcattc gacccgagca ggtctgggcg gctatcgaga aggcttagga cctcgggagg   480
caagttccgg aacgacaaaa tctctgagag agtcgagaca ggtacaccag cctgttcagc   540
tattgcggct tgagtcttgt ctgggctgcg aagcagcagt tcgtcgaact tccgaaactt   600
ctcgaaatcc gttaaatctg actgcataag gttcgcgtag aacgcgcccg tgtcagcctc   660
gtctgaacta agttcgccga gcacgcagcg tatgtgatcg cgcccaagct cgcggtacgc   720
gtctgtccgg tgatgcccgg agacaatctc gaagcctccc gcaggccgag ggcatacaat   780
cacaggatga acgagcttgt tgtgcctgag gttttccctc aattcgacat acttctcggg   840
aggcatgaag cgtctgcggc ctgggacctc atgcagttgg tcgataggca catccactgc   900
gccgccgctg acgcgggccg actcaagttc tgctcttagt tgcgcgatct cgttagcctg   960
tcgctcaacc ttcccttgca tatgcattaa ctgaccgggc gcagttcgcg gcgcttgcgg  1020
accgcgcgca gcggctttct ccaagtcttc cgccgtgacc ttgatgttcc cagcctttgc  1080
ggcaagcttt tctctcaaac tcattcttca attccttgcc aaagcgcgct gaccttgtcg  1140
tccacatagt cgacaaactc atcgcagggt tggcgaatgc gtcgcatcgt ctcggtgttc  1200
gcctcgctag aggagaggtc atagaccgtg cgaaattgaa tgctgctgtt acgggcgagg  1260
tccgtctcag ggatctcaat cggcagcacg cgcgacccat agacgccgcg aatccagtct  1320
gccaccaggc gaggagcgtt ctttttctcc atgcgtgtca tgagaacatc gagaaagtcg  1380
aactcctttt tagatccctc gctctgctct tccatgcctg ttactaggtc cgagaagagt  1440
tgccagaact ggaccataga cgcgaaagcc aaggtgtccg ggaccaccgg tacgatgacg  1500
ccatcggcag cgaaaatcgc gttgatggtc aggtagctga gggtaggagc cgtgtcgagg  1560
atgatgtagt catattcgtc tttcaacgaa tcgaggccgt tacttaacac gcgctcgaac  1620
ggaatatggc cttcctctgc cgtcgcccga gccggaagca taaactccgc gttgaaaagc  1680
tcagtagacg aaggaatcaa atccaggtta ggccagtaag tctcctgagg aagccctcgc  1740
atatcgaagg actcgcccgc caaatacgcc tcgatgagcg gcataatggt gttttcggac  1800
gacacctcgg catgtggatt gatgccatac agcgtggttg cgcttccctg cggatccaga  1860
tcaacgtggc acaccttccg acctcgccgc agactcaagc cctggcagag gagggtggac  1920
atagtggtct tcgtgacacc gcccttgaag ttcgcaactg caatgacttt acctggtccc  1980
cttcgcggga caggcttaag ttccgctcgg atccattgca ttgcctcgct gaggctgaaa  2040
tagcgcactg caccgggtcg cgattgctgg ccctgaggga gatccccctt tttgagggac  2100
```

```
cggttcatcc gcgttttgtc gatgccacac aattcttgta ggcggccaga cgggatcagc    2160
ggggcttcct tccgaggaaa tggctccagc atctcatccc gaattttctg cagcatcacc    2220
gcggagagat ttgccaactg cttcaaatcc tcaggcgtcg tcttgctggg gtgggctagc    2280
ttgatatcca t                                                         2291
```